United States Patent [19]

Latzke

[11] Patent Number: 4,887,368

[45] Date of Patent: Dec. 19, 1989

[54] MEANS FOR STORING AND DISTRIBUTING HEAT AND USE THEREOF

[75] Inventor: Arno Walter Latzke, Zelg-Wolfhalden, Fed. Rep. of Germany

[73] Assignee: Indentor AG, Wolfhalden, Fed. Rep. of Germany

[21] Appl. No.: 239,410

[22] Filed: Sep. 1, 1988

Related U.S. Application Data

[63] Continuation of Ser. No. 157,062, Feb. 2, 1988, abandoned, which is a continuation of Ser. No. 16,500, Feb. 17, 1987, abandoned, which is a continuation of Ser. No. 738,913, May 29, 1985, abandoned.

[30] Foreign Application Priority Data

| May 30, 1984 | [DE] | Fed. Rep. of Germany | 3420121 |
| Jun. 20, 1984 | [DE] | Fed. Rep. of Germany | 3422783 |
| Aug. 27, 1984 | [DE] | Fed. Rep. of Germany | 3431474 |
| Oct. 30, 1984 | [DE] | Fed. Rep. of Germany | 3439727 |
| Mar. 27, 1985 | [EP] | European Pat. Off. | 85 103619.4 |
| Apr. 25, 1985 | [EP] | European Pat. Off. | 85 105047.6 |

[51] Int. Cl.$^4$ ............................................. A43B 13/38
[52] U.S. Cl. ........................................ 36/44; 36/43; 36/98; 128/383
[58] Field of Search ............ 36/43, 44, 107, 98, 36/2.6, 76 C; 128/382, 383, 581, 595

[56] References Cited

U.S. PATENT DOCUMENTS

| 1,659,339 | 2/1928 | Vetterling | 36/44 |
| 1,701,611 | 2/1929 | Glidden et al. | 36/44 |
| 1,815,843 | 7/1931 | Higdem | 36/44 |
| 2,284,947 | 6/1942 | Clifford | 36/44 |
| 2,641,068 | 6/1953 | Thompson | 36/44 |
| 2,736,109 | 2/1956 | Scholl | 36/43 |
| 2,772,196 | 11/1956 | Pooley | 36/44 |
| 3,730,169 | 5/1973 | Fiber | 36/44 |
| 4,055,699 | 10/1977 | Hsiung | 36/44 |
| 4,151,660 | 5/1979 | Yoshimi et al. | 36/44 |
| 4,252,315 | 2/1981 | Kimura | 36/44 |
| 4,263,727 | 4/1981 | Bender et al. | 36/44 |
| 4,331,731 | 5/1982 | Seike et al. | 36/2.6 |
| 4,724,105 | 4/1973 | Weight | 36/44 |

FOREIGN PATENT DOCUMENTS

| 252032 | 5/1926 | United Kingdom | 128/383 |
| 330738 | 6/1930 | United Kingdom | 128/383 |

Primary Examiner—Steven N. Meyers
Attorney, Agent, or Firm—Wegner & Bretschneider

[57] ABSTRACT

Various devices for providing heat insulation and for storing and distributing heat, more specifically body heat, on the areas of the outer skin are described. The devices are formed of a foam layer or a skin compatible layer, a flexible heat conductive metal layer and another foam layer or the like whereby the flexible heat conductive metal layer is placed between the two foam layers or between a foam layer and a skin compatible layer. The devices may be formed in shapes suitable for use as insoles, plasters, soles of shoes, mats, cushions, and the like.

6 Claims, 6 Drawing Sheets

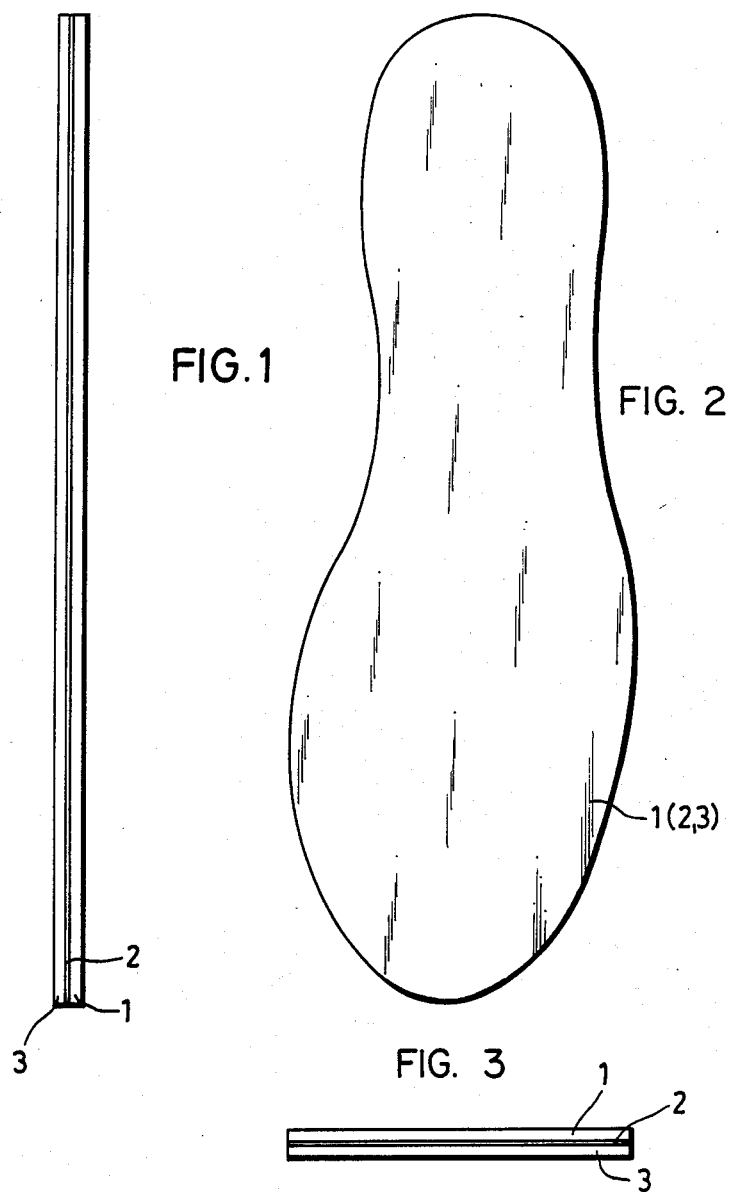

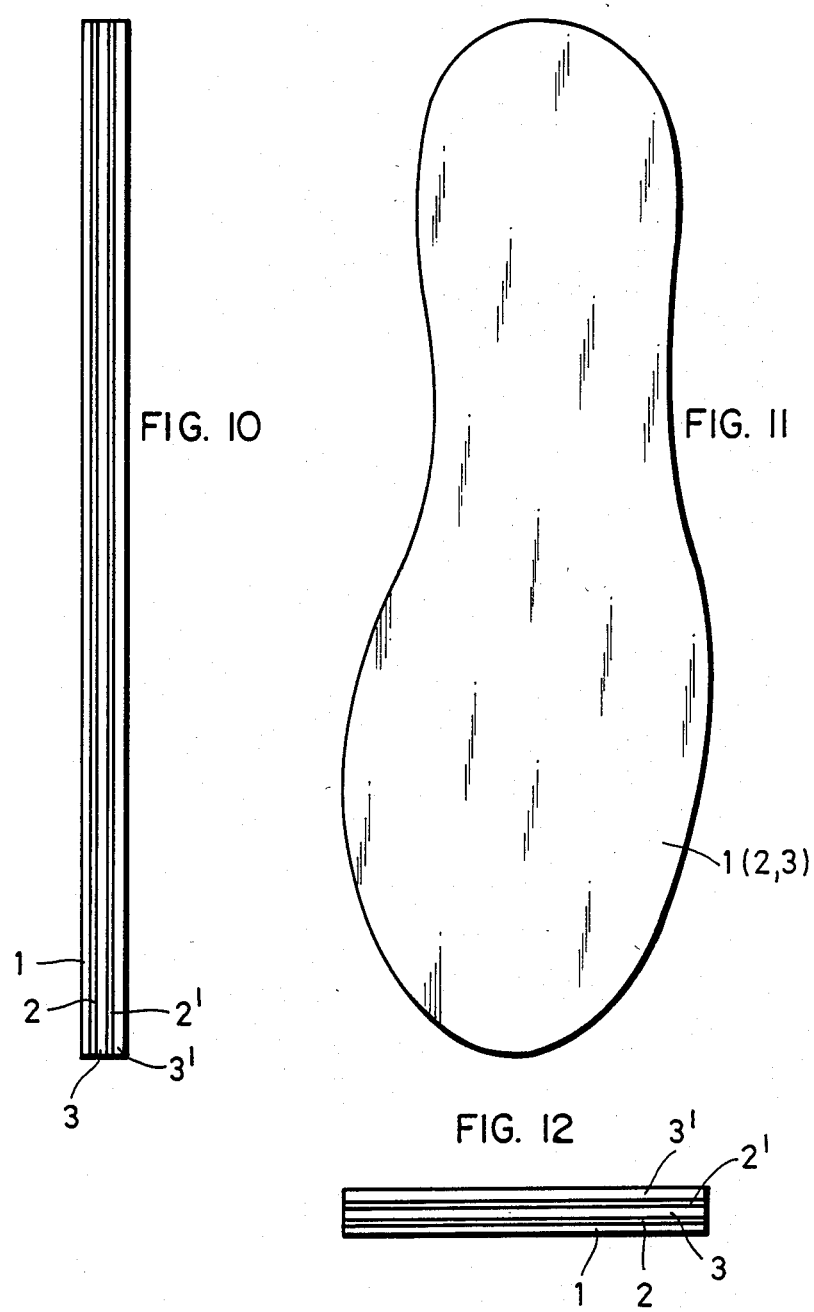

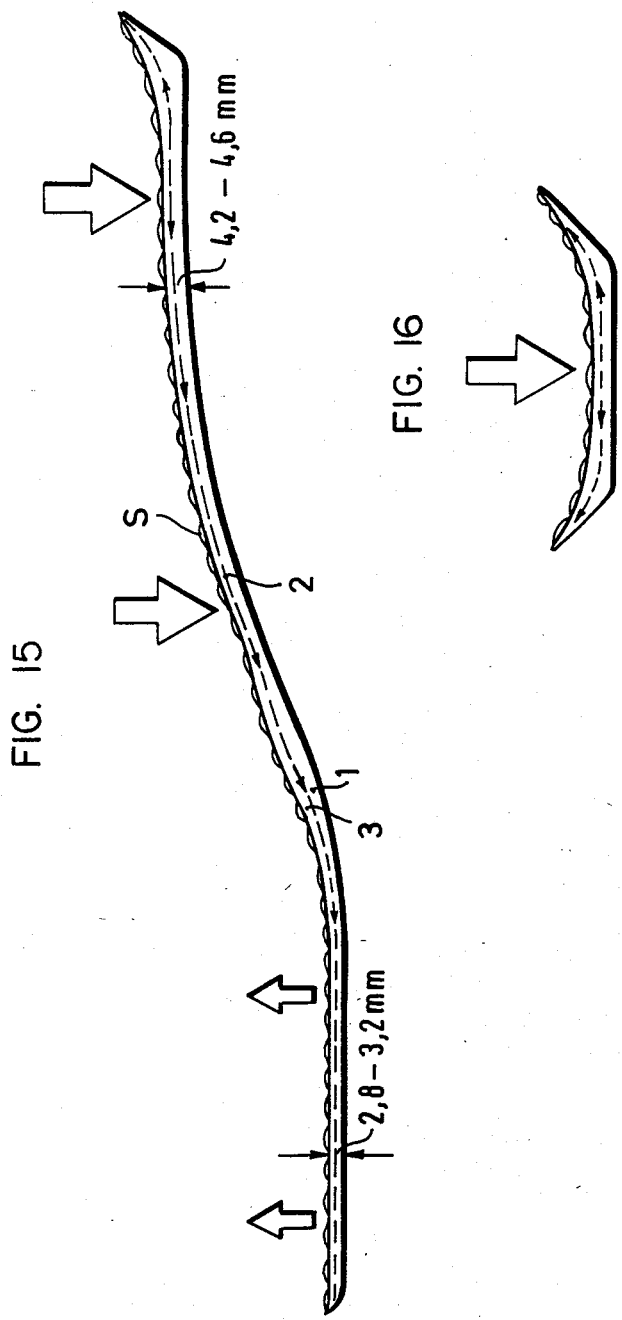

MEANS FOR STORING AND DISTRIBUTING HEAT AND USE THEREOF

This application is a continuation of U.S. application Ser. No. 157,062, which is a continuation of U.S. application Ser. No. 016,500, filed Feb. 17, 1987, now abandoned, which is a continuation of U.S. application Ser. No. 738,913, filed May 29, 1985, now abandoned.

BACKGROUND OF THE INVENTION

The present invention relates to means for effecting heat insulation and for storing and distributing heat, more specifically the body heat on surfaces of the outer skin.

A series of pains, cramps and physical disorders can be caused by insufficient irregular circulation of blood through the outer skin. In many cases alleviance, improvement, or even healing of these pains, cramps, and physical disorders are achieved by the uniform action of heat, and possibly by the joint action of heat and moisture on the effected area. Treatments with infrared radiation, hot-water bottles, heating pads, hot packs and cataplasms usually involve some expenditure and, thus, are not always and readily applicable. Also cold feet result from such effects and can only be insufficiently or inconveniently treated by conventional means.

SUMMARY OF THE INVENTION

It is one object of the present invention to treat the local supercooling and insufficient irregular blood circulation of skin areas in a simple manner. The means therefor should be simple to attach, be not inconvenient to wear, be readily removable and, in addition, be technically uncomplicated and available at a moderate price.

It is another object of the present invention to provide improved means for a general heat insulation that altogether are more stable and durable and will not be ruptured or broken as readily as conventionally used foam layers and foam articles are.

It is a further object of the present invention to develop means for storing and distributing heat, more specifically body heat on surfaces of the outer skin, which means consist of thicker layers of foam material. Namely, in the course of developing the products as mentioned, it has been found that foam layers having a thickness in excess of 4 mm, although they still do excellently store the body heat, do not result in a sufficient distribution on surfaces of the outer skin. Thus, such thicker foam layers cause the occurance of local accumulations of heat as is well-known. However, for certain applications of the new means for storing and distributing heat on surfaces of the outer skin, it is desirable to use foam layers of higher thicknesses as these provide an improved padding and cushioning upon compressive stress.

DETAILED DESCRIPTION OF THE INVENTION

The foregoing objects are attained by means consisting of
(a) a foam layer (1) having a thickness of from 0.8 to 8 mm; or a skin-compatible layer (1) made of a textile fabric, leather, cork or plastics;
(b) a flexible heat-conducting metal layer (2); and
(c) a foam layer having a thickness of from 0.8 to 8 mm, which optionally has been napped.

Accordingly, the present invention provides means for storing and distributing body heat on surfaces of the outer skin comprising
(a) a polyethylene (PE) foam layer (1) of from 0.8 to 4 mm in thickness;
(b) a flexible heat-conducting metal layer (2); and
(c) a further flexible foam layer (3) of from 0.8 to 4 mm in thickness.

The flexible heat-conducting metal layer preferably consists of a foil or a wire net made of aluminum of copper. Aluminum foils are the most inexpensive, although foils or wire nets made of copper have a better heat conductivity. Moreover, nets made of copper wire are capable of bearing a higher mechanical load so that they are preferred to be used in those means which, when worn, will be subject to a greater mechanical stress.

The means according to invention can be shaped, for example, into shoe insoles which, for treating cold feet, are to be inserted into conventional footwear and worn under the outer skin of the sole of the foot. When the means according to the invention are to be attached to other parts of the body, they are preferably fixed on the body surface by using a self-adhesive plaster. Alternatively, rather than using a self-adhesive plaster, they may of course also be held in position by way of a textile bandage or a stocking or sock. Another preferred embodiment has an additional Velcro strip fastener attached on the outer foam layer. The means according to the invention as equipped therewith may be attached to the body in a particularly easy way by using elastic bandages having Velcro strip fasteners themselves.

Eventually, it is possible to apply a skin-compatible self-adhesive layer to one or both of the foam layers which has or have been covered by a removable (strippable) protective film. Prior to use, the protective film is stripped off, and the means is adhered directly onto the skin. If both foam layers each are provided with a self-adhesive layer, then the means can be used twice. If desired the surface facing the skin of the PE foam layer, as well as both of the foam layers, can be covered with a skin-compatible layer of a textile material. This textile layer is capable of conducting heat and absorbing moisture. If it is firmly sealed to the means according to the invention, it may also contribute to affect a further mechanical stabilization of the foam material. As the textile materials, more specifically there may be taken into consideration those made of cotton. Flannel or knitted fabric as well as self-adhesive non-woven fabrics such as, e.g., the product Fixomull Stretch sold by Beiersdorf AG, Hamburg, West Germany, are particularly well suitable.

The means according to the invention are altogether inexpensive, simple, and convenient to wear. All embodiments of the means according to the invention give an excellent storage and distribution onto the underlying areas of the outer skin of the body heat which otherwise would dissipate into the environment. Due to the good compatibility with the skin of polyethylene, the PE foam layers having a thickness from 0.8 to 4 mm, and preferably from 1 to 2 mm, are suitable to store both the emitted heat and the emitted moisture. The flexible heat-conductive intermediate metal layers cause the heat to be uniformly distributed within the means so that skin portions characterized by lower blood circulation will be heated from those skin regions having better blood circulation. The further flexible foam layer having a thickness from 0.8 to 4 mm, and preferably from 1 to 2 mm, provides a heat insulation of the metal layer from the environment and prevents the undesired loss of heat by heat irradiation outwardly from the metal layer. This further foam layer may also consist of PE foam. However, basically other foam materials, such as polyurethane (PU), are suitable as well.

The flexible heat-conductive metal layer has the further advantage in that the means according to the invention altogether are more stable and resistant to wear and does no longer undergo easy rupture or breakage. This effect is already attained by using simple metal foils adhesion-bonded to the foam layers. Means to be used under higher mechnical stress preferably should comprise the metal layer in the form of a wire net. Wire nets made of copper are particularly suitable for this purpose. The metal foils in general have a thickness of at least 0.02 mm, and preferably from 0.08 to 0.3 mm. Weaker foils do not provide sufficient stability and also result in a deteriorated heat conduction from the warmer regions to the colder regions. Thicker metal films, on the other hand, tend to make the means according to the invention more rigid to the extent that it will no longer readily engage to the skin over the whole surface of said means.

If wire nets made of aluminum or copper are used, the wire diameter may be from 0.05 to 0.5 mm. The mesh opening is mostly from 3 to 6 times the wire diameter, while nets having wide mesh openings provide a poorer distribution of the irradiated heat.

When wire nets are employed, there is a chance that the moisture as delivered from the skin surface may evaporate through the foam which has at least partially open pores (partially open-porous or open-celled foam). When metal foils are employed, these act also such as to insulate moisture. Therefore, it is also possible by using these means to subject the skin areas covered therewith to a treatment with moist heat.

In the embodiment of the means according to the invention for use as insoles to be inserted in shoes, the use of metal foils also results in an insulation of moisture so that, on the one hand, no moisture from outside can reach the foot, while, however, on the other hand, the moisture and sweat also cannot escape from the foot. Thus, it will depend on the respective intended use whether the insole embodiment will contain a metal film or a metal wire net as the intermediate heat-conductive metal layer.

Bonding of the metal layer to the two foam layers is effected in a per se known manner by means of conventional adhesives which yield well-adhering bonds to the employed synthetic material as well as to the employed metal. From the view of manufacturing engineering, the use of self-adhering foam webs which are bonded to the metal foils or wire nets is particularly preferred. If wide-mesh wire nets are used, an adhesive contact between the two foam layers may occur whereby the wire net is particularly firmly bonded between the foam layers.

The thickness of the two foam layers may be varied depending on the respective intended use. Thicker foam layers in insoles provide a cushioning action to the sole of the foot and often an additionally desired massage effect.

In an application as means according to the invention for the treatment of the neck and shoulder region, thinner embodiments are preferred, since they will less bulge out and, hence, will provide a better look. Furthermore, for this purpose the embodiments comprising a self-adhesive layer are advantageously usable. For use on the skin of arms and legs, again embodiments are preferred to be used which, in a simple manner, may be attached by use of bandages, stockings etc. or Velcro strip fastener bandages and, thereby, are convenient to wear.

The polyethylene foam as preferred to be used is not only compatible with the skin but also water-resistant so that for hygienic reasons it can be cleaned after use with hot water and a detergent and then be re-used. The same is applicable to the insoles which, in order to remove sweat deposited thereon, may be readily washed and re-used. Also in these procedures, the reinforcing and stabilizing effect of the metal layer is rather beneficial, since the foam layers having thicknesses of from 0.8 to 4 mm (or even taken together of from 1.6 to 8 mm) might be easily ruptured or broken during the cleaning operations. In insoles, of course, the foam layers may additionally be covered with a textile fabric.

It is a particular advantage of the insoles according to the invention that they do well engage to the contours of the foot as well as to the contours inside the shoe and thereby provide an optimum and most direct contact between the sole of the foot and the shoe.

If the outer foam layer also has been made of polyethylene (PE), the means according to the invention can also be used from both sides, one after another, so that the number of required cleaning steps can be reduced.

If both foam layers are to be provided with self-adhesive layers, then PE will, as well, be used as the material for both of the layers.

The means according to the invention can of course be applied not only on the human skin but also on animals, the embodiments comprising bandages, stockings or Velcro strip fasteners being preferred for use on hairy parts of the hide and on pelt.

Further investigation of the means as described hereinabove has resulted in the finding that they are suitable not only for storing and distributing body heat, but also for effecting heat insulation in general. More specifically, it has been shown that the flexible heat-conductive metal layer implies the particular advantage of that the means according to the invention altogether become more stable and resistant to wear and will no longer undergo rupture or breakage as easily as layers do that consist only of foam. Particularly suitable to serve the purpose of heat insulation are those means that consist of two closed-porous PE foam layers adhesion-bonded to an intermediate aluminum foil.

Due to the presence of the aluminum foil, the means according to the invention are not only heat-insulating, but they also act as steam barriers. If, however, it is desired that the insulating material is permeable to steam, then the means according to the invention can be provided with spaced perforations. The perforation holes allow the water vapor to penetrate the means. Nevertheless, the heat insulation is almost completely maintained.

Fields of application for the means according to the invention, thus, are civil engineering and building activities where the means can be used to insulate floors, walls and roofs. Furthermore, it can be employed in automotive assembly, in the textile industry, in the sports articles industry, in the assembly of refrigerators and the like.

Further fields of application are as insulation for swimming pools, pipes, and heating units as well as a general insulation against moisture. The means are further suitable as inserts for paddings and in aircraft construction and shipbuilding. The new means can also be used as disposable sheets and coverings in hospitals, more specifically in the isolation wards thereof, and for patients suffering from strong excretion of liquids.

If the means according to the invention are to be used as means for providing heat insulation in general, a closed-porous foam layer that preferably comprises a self-adhesive layer may be combined with an open-porous foam layer on the surface facing the room. Hereby, in addition, an excellent sound insulation can be accomplished. The self-adhesive layer is preferably covered with a strippable protective film, for example one made of oiled paper, which is removed immediately prior to laying in place. If these layers are to be made permeable to moisture and steam, they are perforated as described above.

Depending on the intended use, the volume weight of the closed-porous PE foam as well as the thickness of the aluminum foil can be varied. In all events, the materials according to the invention can be produced, rolled, stored, transported, and subsequently processed at extraordinarily reasonable costs. Also in the processed state, it continues to have excellent mechanical properties so that it provides the desired heat insulation for a long period of time.

Bonding the PE foams to the aluminum foils is preferably accomplished by using hot-melt adhesives or by flame-laminating. However, basically any other adhesive capable of adhering to aluminum and to polyethylene can be used.

If an aeration is necessary, the means according to the invention will be perforated. The holes are preferably spaced apart from each other at distances of from 10 to 20 mm. Then, the hole dimensions preferably range between 1 and 5 mm in diameter.

The volume weights of the PE foams used may be subject to variations within wide limits. They may be between 20 and 150 kg/m$^3$. For insoles, volume weights between 30 and 120 kg/m$^3$ have proven to be particularly useful. For use as mere heat insulation material with low mechanical stress, there may also be used lower volume densities. In cases of higher stress, it is recommended to employ higher volume densities. Another criterion for the selection is the demanded degree of heat insulation. In particular cases such as a use for insoles, it may be advantageous that pre-fabricated laminates are subsequently molded under the action of heat and pressure and thereby the volume density of the material is increased.

Further investigation of the means as described hereinabove has resulted in the finding that a further improvement can be accomplished by replacing the foam layer (1) facing the skin with a skin-compatible layer made of textile fabric, leather, cork or plastics, so that the flexible heat-conductive metal layer (2) is brought into contact with the outer skin without a heat-insulating PE foam layer being present. Hereby, the heat as emitted from the body surface is distributed more rapidly and more uniformly, and any local accumulation of heat is avoided. The storage of the heat having been uniformly distributed then is again effected by the flexible foam layer (3) having a thickness of from 0.8 to 4 mm.

More specifically, if the means according to the invention are to be used as insoles or as an integrated constituent of a sole of a shoe, it has proven to be particularly expedient to provide a further flexible heat-conductive metal layer (2') and a further flexible foam layer (3') made of closed-porous polyethylene foam and having a thickness of from 0.8 to 4 mm contiguous to the foam layer (3).

Such insoles or constituents of a sole of a shoe according to the invention have the following essential advantages:

1. A uniform constant surface temperature of the foot contact surface is obtained and rapidly adjusted. The heat as delivered from the foot contact surface is stored to an optimum degree and, thus, the feet durably and all over will feel comfortably warm.
2. Surprisingly, the uniform warming of the sole of the foot results in a reduced production of sweat, so that the foot contact surface has a lower degree of moisture.
3. Insoles according to the invention have a deformation corresponding to the form of the foot, which gives an explicitly pleasant feeling.
4. The sole thickness is astonishingly small; however it provides effects which so far have not been accomplished by using substantially thicker materials.

The particular reasons herefor are that, according to the present invention, for the first time a good heat conductor has been combined with a heat insulator. A combination of these two entirely different types of materials has so far never been contemplated by the artisan who, in order to achieve good heat insulation, has only used heat insulators and has avoided a use of good heat-conductive materials. The combination, which indeed appears as a paradox, for the first time causes not only a good heat storage, but also a good heat distribution over the area to be treated. Thereby, a buildup of local superheating and local supercooling is either prevented from occurring at all or is rapidly levelled down. However, just these effects of local superheating and local supercooling are known to be causes for pains, strained muscles, local sweat formations, and so-called "burning feet". Thus, the use of the means according to the invention in shoe soles provides for the first time a solution to the problem of the optimum shoe sole, a solution that has long been sought. So far, all shoe soles in use either were insufficient with respect to heat insulation so that they yielded cold feet, or they did so well insulate the heat that local superheating effects, e.g. sweating feet and burning feet, were caused.

Since, for insoles and soles of shoes, a closed-porous polyethylene foam is preferred to be used, this foam cannot become filled with water or sweat, that is not even from the cut edges. Thus, the means according to the invention as to their effect are impaired neither by internal nor by external moisture. This is why the used materials also cannot be attacked by microorganisms such as bacteria and fungi so that they retain a neutral odor and do not bind alien odors. They are not damaged either by soap water nor by washing machines and, thus, can be easily cleaned if desired. Thus, they meet the hygiene standards of today as set for insoles and soles.

By a suitable selection of the volume weights of the employed foams, some permanent deformation can be accomplished which ensures a natural engagement of the insole or sole, respectively, to the individual surfaces of the sole of the foot. This provides an optimum comfort and pleasant feeling to the wearer.

By the use of two flexible heat-conductive metal layers (2) and (2') and of the two foam layers (3) and (3') contiguous thereto, there have been formed two "heat chambers" with an optimum insulation and an optimum distribution of the heat, and shielding of the cold, respectively, is effected by the shoe sole. Measurements on such insoles according to the present invention have shown that, even in the case of larger temperature differences sensed on the one side, only minimal temperature differences can be determined on the other side, whereas all prior art materials, even those having a higher insulating power, cause higher temperature variations on the other side of the layer as well. This holds for insulating materials quite generally and for all previously known insoles and soles of shoes in particular.

The means according to the present invention are also effective when applied to other parts of the outer skin. Thus, these means can be applied onto the skin in the form of plasters designed into various shapes and thereon can display their pleasant alleviating or even healing effects. Thus, such plasters can be attached to the body by means of a self-adhesive plaster. Instead of using a self-adhesive plaster, they may of course also be attached by means of a textile bandage or a stocking or sock. Another preferred embodiment additionally has a Velcro strip fastener provided on the outer foam layer. The means in accordance with this embodiment may be most readily attached by means of an elastic bandage having a Velcro strip fastener. Eventually, it is also possible to apply a skin-compatible self-adhesive layer which has been covered by a removable protective film onto the skin-compatible layer (1). Prior to use, the protective film is stripped, and the means is directly adhered to the skin. If desired, it is possible to impregnate the skin-compatible layer (1) with substances promoting blood circulation, more specifically those which have already proven to be valuable in conventional medical plasters. These substances promoting blood circulation include substances from mustard, paprica or *Fructus Capsici*, which are incorporated in these layers in amounts of from 0.5 to 5% by weight.

For the skin-compatible layer (1), all skin-compatible textile fabrics, leather, cork or synthetic materials can be employed. Particularly preferred is the use of woven or knitted textile fabrics made of cotton, wool, polyamides, polyesters, and regenerated cellulose. More specifically, if the means according to the invention are incorporated in shoe soles, leather, cork or skin-compatible plastics layers may also be employed. Such a skin-compatible layer in general does not have any heat-insulating property by itself, so that the heat emitted by the body surface is rapidly conveyed to the flexible heat-conductive metal layer and can be re-distributed there. This is not, or only to a lower degree, applicable in the case where a polyethylene foam layer is employed, so that then still some local heat accumulation may be observed. This, in the usual manner, will result in sweat formation, burning feet and a non-optimized re-distribution of the heat. The local temperature differences will at least still be sensed as unpleasant, so that subjectively the means of the latter embodiment of the present invention will be perceived as being more pleasant.

Again the flexible heat-conductive metal layer preferably consists of a foil or a wire net of aluminum or of copper. Aluminum foils are the most inexpensive and most easily to be processed, so that they are particularly preferred. Basically, it is as well possible to use plastics films having a sufficiently thick metal layer thereon which has been applied by vapor deposition. However, the metal layers must be thick enough such as to be capable of laterally carrying away the heat.

The flexible foam layers of from 0.8 to 4 mm in thickness preferably consist of closed-porous polyethylene foam, since this foam material is available at a particularly reasonable price, has good insulating properties, has good mechanical qualities, and does not result in any undesired uptake of moisture and liquid. However, basically any other foams such as, for example, PU (polyurethane) are suitable.

Another advantage of the layers having been bonded to one another according to the present invention is the increased stability and wear resistance, so that the means according to the invention will rupture or break less readily than the individual components do.

If desired, it will of course be possible that the means of this latter embodiment in addition are perforated or slotted in order to render them permeable to moisture and water vapor. The heat insulation and heat distribution nevertheless is almost completely retained.

These means can be used for general heat insulation purposes in the same manner as the means described before.

Moreover, in the course of further developing the products of the invention, it has been found that foam layers the thickness of which is more than 4 mm, although they still do excellently store the body heat, do not result in a sufficient distribution on surfaces of the external skin. Such thicker foam layers again allow the known heat accumulation to occur. However, for some applications of the new means for storing and distributing heat on surfaces of the outer skin, it is desirable to employ the thicker foam layers, since these provide an improved padding and cushioning effect upon compression stress.

It has been found that means are suitable which consist of
(a) a closed-porous foam layer (1) of from 2 to 8 mm in thickness;
(b) a flexible heat-conducting metal layer (2); and
(c) a further closed-porous foam layer (3) of from 2 to 8 mm in thickness,
wherein one or both foam layers (1) and (3) are surface texturized on their outer surface(s). The texturized surface must be that of the side coming into contact with the outer skin. The surface texture is preferably formed by parallel and crossing lines of trapezoid-shaped notches 0.8 to 3 mm in depth and spaced apart at distances from 3 to 12 mm, the depth of the notches being from 20 to 50% of the thickness of the foam layer, and the width of the notches being from 10 to 30% of the surfaces of the naps.

Such texturized surfaces do no longer allow the undesired accumulation of heat to occur, since the notches result in some distribution of the heat over the areals of the outer skin. It is to be taken care of that the predominant part of the surface of the foam will remain planar so that only a minor part affects the heat to be distributed through the notches. If the portions of the smooth surface decrease below 70%, this will result, on the one hand, in the occurence of undesired straining points which give an unpleasant feeling and, on the other hand, in an insufficient storage of heat.

The depth of the notches should be within the range of between 20 and 50% of the thickness of the foam layer.

Less deep notches will negatively affect the heat distribution such as to become insufficient, while deeper notches will significantly lower the mechanical strength.

The texturizing procedure is preferred to be carried out under action of heat and pressure by using a pertinent heated roll. The heat and pressure treatment results in some compression of the surface region of the foam layer, which will improve the mechanical properties of the means according to the invention. Thus, the means according to the invention are napped to appear waffle-like. The surface is preferably formed by raised triangles, squares or hexagons, depending on the arrangement of the parallel and crossed lines of notches.

If the means according to the invention are only texturized on one surface thereof, they tend to get warped. Therefore, it is preferred that both surfaces be texturized so that the products formed thereby remain smooth and in plane and do not get warped or rolled.

The foam used in the means according to the present invention preferably is closed-porous PE soft foam. However, bascically other closed-porous foams, particularly soft foams (high-resilient foams) are suitable as well.

The flexible metal layer again consists of a foil or of a wire net, for example, one made of aluminum or copper. Aluminum foils are particularly preferred.

The new means according to the invention are particularly suitable as soles of sandals or as cushions, mats or bed overlay.

Also these means according to the present invention are hygienic and can be cleaned in a simple manner. Due to the thicker foam layer, they have an improved padding effect and thus give a more pleasant feeling than smooth but thinner products.

Baby mats preferably are covered with a fabric on the one surface thereof and coated with a washable layer of plastics such as PVC on the other surface thereof. They are suitable for the playing and lying as well as for being swaddled.

In the use of the means according to the invention as soles of sandals, it has proven to be beneficial only to nap the surface facing the skin in accordance with the invention, while the opposite surface of the sole is only roughened to the degree that it will better adhere to the floor such as to avoid an undesired slipping. For simplicity's sake, it is also readily possible to nap the surface facing the floor of the sole as well.

The further development of the insoles has shown that insoles, but also components of soles in shoes, boots, sandals, sport shoes etc. can be further improved if they consist of
(a) a closed-porous polyethylene foam layer (1) having a thickness of originally from 2 to 8 mm (and preferably from 3 to 5 mm);
(b) a flexible heat-conductive metal layer (2) having a thickness of from 0.02 to 0.08 mm (and preferably from 0.03 to 0.05 mm);
(c) a closed-porous polyethylene foam layer (3) having a thickness of originally from 2 to 8 mm (and preferably from 3 to 5 mm); and
(d) a skin-compatible layer of a textile fabric (S), all of the layers (1), (2), (3) and (S) having been laminated to adhere firmly together, and the laminates by the action of heat and pressure, having been orthopedically molded in the middle foot and heel region, flatly compressed in the forefoot region and provided with surface texture in the areas of the layers (3) and (S).

Again aluminum is preferred for the metal layer. The textile layer S preferably consists of cotton tricot fabric.

The orthopedic molding, more particularly, consists of a lateral lifting in the heel region, a bulging in the inner region of the middle foot, and preferably is significantly "broken-up". Broken-up is understood to mean an S-shaped deformation by which the heel region comes to be situated significantly higher than the forefoot region. This orthopedic deformation and break-up results in a particularly high wearing comfort and at the same time a permanent engagement of the insole to the sole of the footwear. This is of particular importance for ladies' shoes, more specifically if they have superhigh heels. Thus, the insoles according to the invention are best suited for pumps.

A particularity of the insoles according to the invention consists of that after orthopedic molding, pressing and texturizing, the thickness of the laminate in the forefoot region is smaller than in the middlefoot and heel regions. Due to the higher compression, although the heat insulation is lowered, the wearing comfort is increased. However, the texturizing on the surface, on the one hand, and the metal film in the intermediate range, on the other hand, surprisingly cause the forefoot to be well and uniformly heated, while it has been shown that the excess heat from the heel and middlefoot regions is conducted to the forefoot region.

Surface texturizing results in a microcirculation of air and moisture, on the one hand, and in a massage effect promoting blood circulation, on the other hand. In the insoles as molded with the action of heat and pressure, compressed and napped according to the invention, these effects are greater than in untreated laminates. Comparative measurements indicate that the deformation from spherical form to lenticular form of the gas bubbles in the closed-porous polyethylene foam under the action of heat and pressure is of crucial influence. Furthermore, this permanent deformation under the action of heat and pressure yields to an increased stability in shape under long-term stress of the insoles so that the use-life thereof is significantly extended.

The orthopedic deformation not only increases the wearing comfort but also the improved drain of redistribution, respectively, of heat from the heel and middlefoot region to the forefoot region where the heat insulation has per se been lowered due to the compression to make a flat layer according to the invention.

The skin-compatible textile layer (S) also contributes to increase the wearing comfort. Moreover, it enables the air and moisture distribution to be improved.

More accurate measurements of the insoles modified according to the invention have further shown that, due to the higher compression, the heat insulation in the texturized area (3) and (S) is less than that on the other side of the metal foil in the area (1). This means that the lower un-texturized foam layer (1) predominantly shields the foot from higher temperature deviations, i.e. from cold in winter and from heat in summer. The metal layer (2) causes a re-distribution of local temperature differences to occur. The upper compressed foam layer also provides some heat insulation, more specifically a heat exchange at the sole of the foot in the microrange between the individual naps. The nap formation causes some massage effect to be obtained, more specifically when the foot is loaded and relieved from load, whereby the blood circulation is promoted.

Comparative measurements using a commercially available insole consisting of a textile fabric layer, two different foam layers, and a lattice film comprising vapor-deposited aluminum have shown that, upon point-focal heat supply, the heat insulation is improved by about the factor of 10. Thus, in order to obtain protection from cold in winter, it was required to use thicker insoles. However, such thicker insoles in summer caused an increased sweat formation and burning feet. Thus, the insoles according to the invention for the first time can be used in summer and in winter at same thickness and all over the year provide an optimum wearing comfort.

More particularly, the effect resides in that, according to the invention, for the first time a good heat conductor has been combined with a good heat insulator. In the improved insoles according to the invention, this effect is even enhanced by the skin-compatible textile fabric layer (S), which together with the layer (3), has been texturized and, thus, has been particularly highly compressed, improving the air and moisture circulation in the napped area and the orthopedic shaping in the middlefoot and heel region of the laminates. The reduced heat insulation according to the invention in the forefoot region surprisingly is compensated by the good heat conductivity of the metal layer. The compression to form a flat sole part in the forefoot region allows particularly thin insoles to be manufactured, more particularly for ladies' footwear.

Of course, it will be possible to make these insoles also into permanent components of shoes. To this end, they are prefabricated and adhesion-bonded to the soles of conventional shoes, boots, sandals, etc. As polyethylene foam in general is very difficult to be permanently bonded, it is recommended that also the bottom side of such sole components is laminated with a textile fabric layer which then is bonded to the inner sole of the footwear.

The manufacture of the insoles according to the invention is preferably effected by previously bonding the skin-compatible textile fabric layer and, optionally, the textile fabric layer desired to be present at the bottom for bonding sole components, to the respective polyethylene foam layer(s). This is possible in a particularly simple manner by flame bonding. Of course it is also possible to apply these materials by means of adhesives. Herefor there are suitable thermo-adhesives or hot-melt adhesives having sufficient resilience and permanent stability under load.

After the pre-manufactured laminates have been prepared from the layers (1), (2), (3) and (S), they are molded at a temperature from 120° C. to 170° C. under pressure, compressed and texturized, preferably in a single step. After having been pressure-molded, compressed, and texturized, the laminates still have from 20 to 80% of the initial thickness. Basically, although it would be possible to start with a material previously provided with a surface texture, the surface texture would at least partially be lost again in the subsequent orthopedic deformation and compression to make the flat sole part. In contrast to conventional insoles, the insoles according to the invention are no longer flat, but have been given an orthopedic shape and, in a preferred embodiment, are even broken up as mentioned above.

BRIEF DESCRIPTION OF THE DRAWINGS

Some preferred embodiments of the present invention are further illustrated in closer detail with reference to the accompanying drawings wherein FIG. 1 is a side elevation of a first preferred embodiment of an insole constructed according to the invention;

FIG. 2 is a top elevation of the FIG. 1 embodiment;

FIG. 3 is an end elevation of the FIG. 1 embodiment;

FIG. 10 is a side elevation of a second preferred embodiment of an insole constructed according to the invention;

FIG. 11 is a top elevation of the FIG. 10 embodiment;

FIG. 12 is an end elevation of the FIG. 10 embodiment;

FIG. 15 is a sectional side view illustrating the FIG. 1 embodiment formed into an orthopedically molded insole; and FIG. 16 is a sectional view in the transverse direction of the FIG. 15 embodiment.

Figure 4:
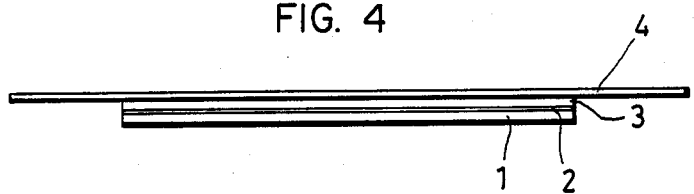
FIG. 4 is an end elevation of a preferred embodiment of a self adhesive plaster constructed according to the invention.
Figure 5:
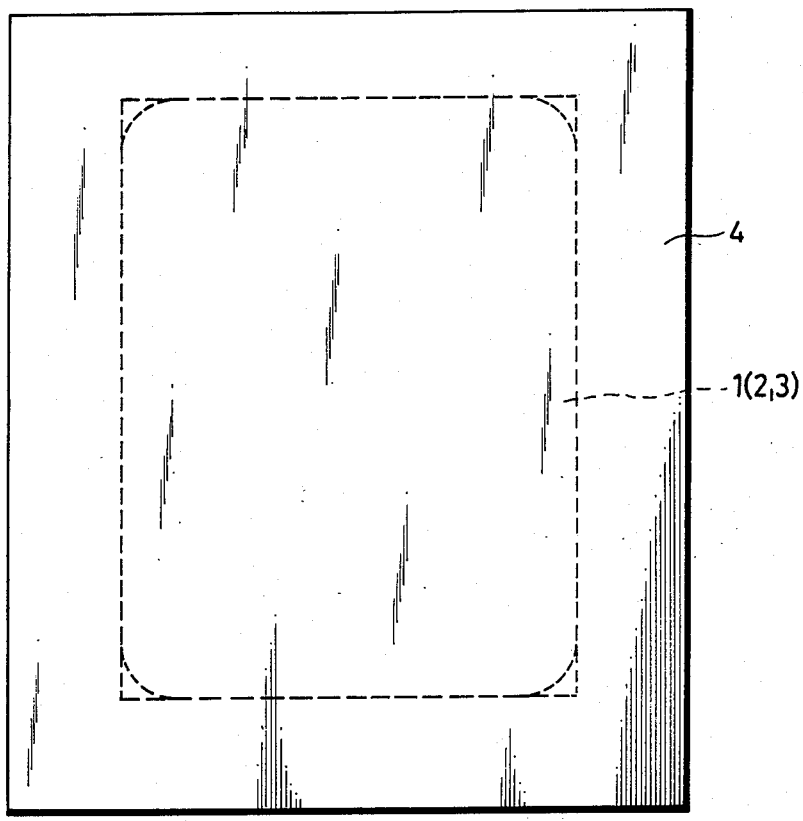
FIG. 5 is a top elevation of the FIG. 4 embodiment.
Figure 6:
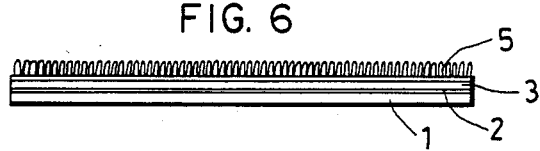
FIG. 6 is a second preferred embodiment of a plaster or the like constructed according to the invention and having a Velcro strip fastener.
Figure 7:
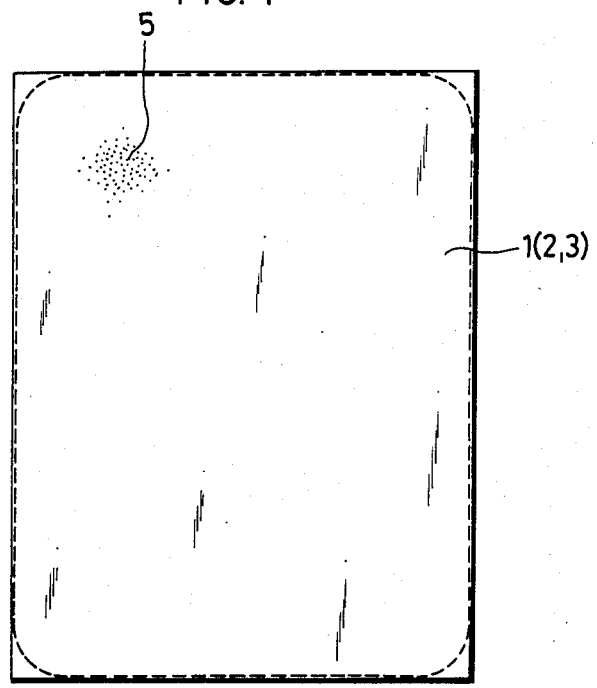
FIG. 7 is a top elevation of the FIG. 6 embodiment.
Figure 8:
FIG. 8 is a sectional view of a second preferred form of the invention wherein the intermediate layer is formed of a wire net.
Figure 9:
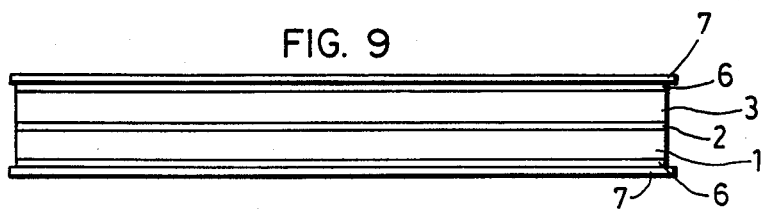
FIG. 9 is a sectional view of a third preferred form of the invention comprising a skin compatible soft adhesive layers and removable protection films on both sides thereof.
Figure 13:
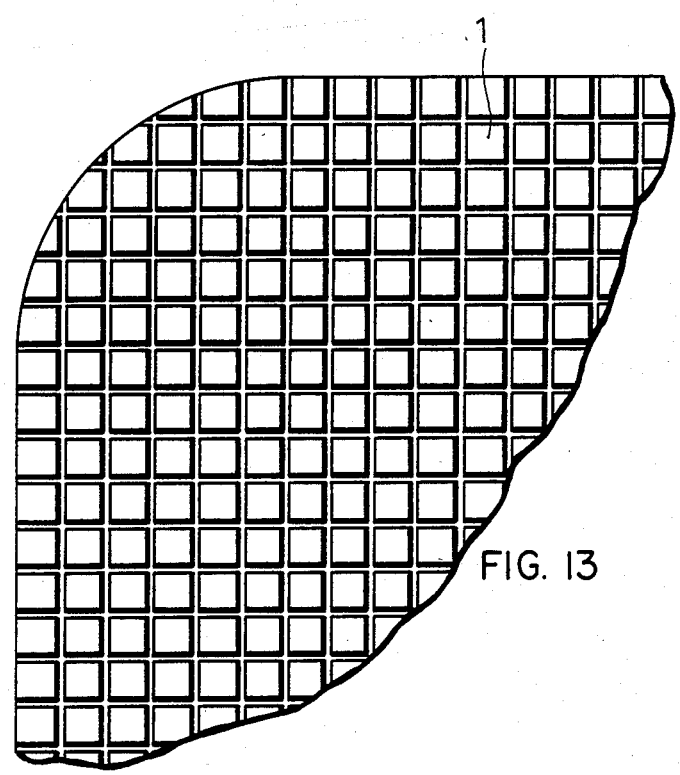
FIG. 13 illustrates a fourth preferred form of the invention in partial view as a rectangular cushion having rounded corners.
Figure 14:
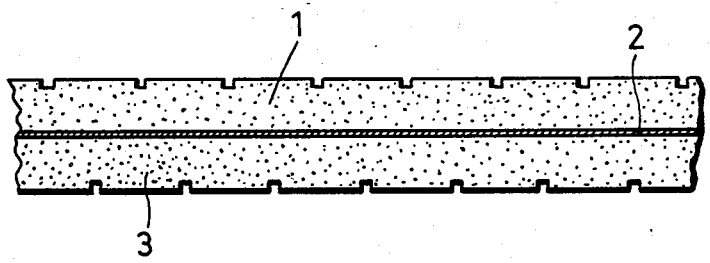
FIG. 14 is a sectional view of the FIG. 13 embodiment.

In the Figs., the reference numerals have the meanings as defined hereinbelow:

1. PE foam layer or a skin-compatible layer made of textile fabric, leather, cork or plastics;
2. metal layer;
2'. a further metal layer;
3. the further flexible foam layer;
3'. a further foam layer consisting of a closed porous PE foam;
4. a self-adhesive plaster;
5. a Velcro strip fastener;
6. a self-adhesive layer;
7. a removable protective film;
8. a napped foam layer; and
S a layer of a textile material.

One preferred embodiment of the insole according to the invention as shown in FIG. 10, for example, comprises the components 1. layer made of highly absorbing cotton fabric;
2. metal layer consisting of an aluminum foil of 20 $\mu$m in thickness;
3. layer of a closed-porous polyethylene foam having a thickness of 2 mm and a volume weight of 67 kg/m$^3$;
2'. layer again consisting of an aluminum foil having a thickness of 20 $\mu$m; and 3'. layer of closed-porous polyethylene foam having a thickness of 1 mm and a volume weight of 100 kg/m$^3$. Besides, the foam layer 3' is colored and thus readily distinguishable from the bright surface of the cotton fabric. Hereby it is ensured that the insole is always in the correct position inserted in the shoe.

In a plaster according to the invention, the numerals accordingly denote the layers 1. layer made of a cotton fabric;
2. layer made of an aluminum foil having a thickness of 30 μm; and
3. layer of closed-porous polyethylene foam having a thickness of 3 mm and a volume weight of 30 kg/m$^3$.

Comparative temperature measurements carried out with products according to the invention and with a commercially available product consisting of a textile fabric, a layer of open-porous foam, a layer of closed-porous foam, and a plastics film bearing an aluminum layer vapor-deposited thereon revealed that with an initial local temperature difference of 5.6° C. at a distance of 2 cm on one side of the test specimens, the respective temperature difference on the reverse side of the insole according to the invention was just 0.1° C., whereas the temperature difference measured on the reverse side of the commercially available insole was still 0.7° C. In contrast to the insole according to the present invention, in the commercial product the plastics film bearing the aluminum layer vapor-deposited thereon is on the surface remote from the skin, while according to the invention the well heat-conducting aluminum foil is immediately beneath the textile layer. The total thickness of the insole according to the invention is little more than 3 mm, whereas the commercial product is 5.5 mm in thickness.

In another preferred embodiment, the surface is texturized in the form of parallel notches perpendicular to one another at distances of 7 mm. The notches are trapezoidal in shape with a top width of 2 mm, a bottom width of 1 mm, and a depth of 1.5 cm. The foam layer has a regular thickness of 5 mm and, thus, is 3.5 mm in thickness at the bottom of the notches. The aluminum foil is 30 μm in thickness. The material on both sides is a closed-porous PE soft foam having a volume weight of 50 kg/m$^3$.

The material may be inked in different colors in the upper and lower foam layers. Sandals are formed by that in the front part a fabric or foam strap of suitable size is turned over and is either adhesion-bonded between the two layers or laterally attached by fusion or adhesion-bonding, respectively. The sole surface may be surface texturized in the same manner or be provided with a finer profile.

In FIG. 17, the larger arrows in the heel and middlefoot regions indicate the heat flow from the foot into the insole. The smaller arrows in the forefoot region indicate that there heat is delivered from the insole to the foot. The surface facing the sole of the foot preferably is provided with naps in a square or rhomboid pattern, the naps being spaced apart by about 5 mm and in the form of wedge-shaped indents of about from 0.5 to 1 mm.

As the starting materials, there were used for the polyethylene foam layers (1) and (3) self-adhesive layers of 3 mm in thickness, namely made of polyethylene foam No. 1503 of the Company of Alveo. having an original volume weight of 67 kg/m$^3$. In the finished insole the thickness of the total laminate is still from 2.8 to 3.2 mm in the forefoot part and from 4.2 to 4.6 mm in the heel part. In the edge and margin zones, the thickness of the polyethylene foam layer (1) is even more than 3 mm.

It will be apparent from the sectional view in the longitudinal direction that the insole has been shaped in to an S curve and, thus, is broken up.

It will be apparent from the cross-sectional view that the lower foam layer (1) is smooth and is well suitable to be adapted to the sole of a shoe. In contrast, the side edges of the insoles have been elevated and are tapered in wedge-shape so that, in the orthopedic deformation, they provide a particularly pleasant sensation of wearing.

In this embodiment, the metal layer (2) consists of an aluminum foil having a thickness of 40 μm. Optionally, said aluminum foil may be perforated so that, upon pressure and heat molding, a gas exchange will be possible. In addition, the foam layers (1) and (3) may be perforated as well.

What is claimed is:

1. A device for storing and distributing heat on areas of the outer surfaces of human skin, comprising:
    a pair of closed porous polyethylene foam layers, each having a thickness of from 0.8 to 8 mm;
    a flexible heat conductive metal layer interposed between said foam layers and having a thickness of 0.02 to 0.08 mm, said metal layer being made of a material selected from the group consisting of aluminum and copper;
    a skin compatible layer of textile fabric laminated to an entire outer surface of one of said foam layers wherein said skin compatible layer is the top-most layer such that said skin compatible layer comes into direct contact with the skin of the user; and
    means for attaching the device to the skin;
    wherein said foam layers are laminated to adhere firmly together;
    wherein said skin compatible layer is impregnated with a substance which promotes blood circulation when this substance comes into contact with the skin of the user.

2. A device as claimed in claim 1, wherein said metal layer is made from aluminum foil.

3. A device as claimed in claim 1, having the form of a cushion.

4. A device as claimed in claim 3, wherein said skin-compatible layer is surface texturized.

5. A device as claimed in claim 1, having the form of a mat.

6. A device as claimed in claim 1, having the form of a bed-overlay.

* * * * *